US 6,706,279 B1

(12) United States Patent
Hazzi

(10) Patent No.: US 6,706,279 B1
(45) Date of Patent: Mar. 16, 2004

(54) WOUND DRESSING

(75) Inventor: Nabil Hazzi, Sainte-Foy (CA)

(73) Assignee: Pharma Mag Inc., Sainte-Foy (CA)

( * ) Notice: Subject to any disclaimer, the term of this patent is extended or adjusted under 35 U.S.C. 154(b) by 6 days.

(21) Appl. No.: 09/696,297

(22) Filed: Oct. 26, 2000

(51) Int. Cl.⁷ .............................. A61K 9/70; A61F 13/00
(52) U.S. Cl. ..................... 424/443; 424/445; 424/447; 424/449
(58) Field of Search ................. 424/443, 445, 424/400, 449, 447

(56) References Cited

U.S. PATENT DOCUMENTS

| | | | |
|---|---|---|---|
| 4,948,575 A | | 8/1990 | Cole et al. |
| 4,960,413 A | | 10/1990 | Sagar et al. |
| 5,084,281 A | * | 1/1992 | Dillon .................. 424/677 |
| 5,238,685 A | * | 8/1993 | Wren .................. 424/443 |
| 5,468,492 A | * | 11/1995 | Szaloki et al. ............. 424/70.1 |
| 5,482,932 A | * | 1/1996 | Thompson ............... 424/443 |
| 5,814,032 A | * | 9/1998 | Hori et al. .................. 604/307 |
| 5,998,692 A | | 12/1999 | Gilding |
| 6,348,212 B2 | * | 2/2002 | Hymes et al. ............. 424/400 |

FOREIGN PATENT DOCUMENTS

| | | |
|---|---|---|
| GB | A-0415042 | 8/1934 |
| GB | A-0568177 | 3/1945 |

* cited by examiner

*Primary Examiner*—Thurman K. Page
*Assistant Examiner*—Robert M. Joynes
(74) *Attorney, Agent, or Firm*—Goudreau Gage Dubuc

(57) ABSTRACT

Provided herein is a disinfectant wound dressing for treating tissue wounds, said dressing comprising a hydrogel matrix including an absorbent fibrous material comprising alginate salt, said hydrogel matrix being loaded with absorbed components comprising a hydrocolloid moisture retaining component, a salt component compatible with the tissue being treated, and a vulnerary polysacharide component being therapeutically acceptable with regard to wound tissue irritation level and systemic toxicity level. The wound dressing will optionally contain a further disinfectant component.

5 Claims, No Drawings

WOUND DRESSING

BACKGROUND OF THE INVENTION

1. Field of Invention

The present invention relates to wound dressings.

2. The Prior Art

It is desirable to control the condition of a wound to encourage the healing process. One way is to maintain the wound sufficiently moist so as to absorb or to eliminate the formation of dry crusty scar tissue at the wound site. Another way is to absorb fluids and materials exuded from the wound, including dead leucocytes, epidermal and dermal cells.

At the same time, it is desirable to prevent contamination of the wound by external agents, whether bacterial or fungal, which can lead to infection. Examples of wounds to which these factors are relevant are ulcers, traumatic and surgical wounds, burns and tissue donor sites.

Traditionally, wounded tissues have been covered with various ointments and gauzes. However, these treatments do not shield the wound from external contamination, do not sufficiently retain moisture, and gauzes often become embedded in the wound tissue causing damage and pain when wound dressings are changed.

A recent approach has been to use various forms of hydrogels as wound dressings. The term hydrogel refers to water absorbing gel substances of varying rigidity. Hydrogels may be loaded with various liquid or solid substances destined to hasten and facilitate wound healing. Hydrogels of least rigidity are often administered by syringe while more rigid hydrogels are packed in sterile sachets opened immediately prior to disposing the hydrogel on the wound.

One type of hydrogel wound dressing is a hydrogel consisting of alginate fibres. These are now known in the art. For example, U.S. Pat. Nos. 4,960,413, 4,948,575, 5,238,685 and 5,998,692 provide wound dressing materials containing alginate fibres.

Also known is the therapeutic value of sterilised seawater solutions on open wounds. For example, U.S. Pat. No. 5,084,281 provides a method for treating tissue wounds with a seawater solution.

However, there remains a need for an improved hydrogel wound dressing which is malleable, biodegradable and loaded with various components aimed at preventing infection and facilitating wound healing.

SUMMARY OF THE INVENTION

In general terms, the invention provides a wound dressing for treating tissue wounds, the dressing comprising a hydrogel matrix including an absorbent fibrous material comprising an alginate salt, said hydrogel matrix being loaded with components comprising:

a hydrocolloid moisture retaining component;

a salt component compatible with the tissue being treated; and a vulnerary polysaccharide component.

Preferably, the hydrogel dressing of the present invention will also include a further disinfectant component and will be provided in sheets.

Further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

DETAILED DESCRIPTION OF THE PREFERRED EMBODIMENT

A detailed description of a preferred embodiment of the present invention will now be described for the purpose of illustration.

The wound dressing of the present invention is a hydrogel loaded with various components for hastening and facilitating wound healing while preventing infection. The hydrogel comprises a matrix of absorbent fibrous material comprising an alginate hydrogel, said matrix being loaded with components comprising:

a hydrocolloid moisture retaining component;

a salt component compatible with the tissue being treated;

a vulnerary polysaccharide component; and optionally a further disinfectant component.

In the present invention, the term "disinfectant" is synonymous with the terms "antiseptic" and "anti-bacterial". Also, the term "loaded" refers to components being absorbed in the hydrogel matrix or to components being deposited on the surface of the hydrogel matrix such as by evaporating a solution containing the component.

Also, the weight percentages (wt %), unless otherwise stated are based on the wt % of ingredients used in the process of making the dressing and not those present in the final product. The proportions were established for a process in which approximately 80% water was incorporated. The dressing may however by dried in order to lower the water content which in turn has a direct effect on the concentration of the other ingredients present in the dressing. The final proportion of water present in the dressing will vary according to the cohesiveness and malleability properties sought after which will differ according to the ingredients used and their concentration.

The process for making the dressing and each ingredient of the wound dressing will now be described in further detail.

The framework of the wound dressing is a matrix composed of either sodium or calcium alginate or a combination of both. Alginate is a naturally occurring protein generally extracted from sea weeds. Upon reacting alginate with sodium or calcium species, insoluble fibers are formed. Various proportions of sodium or calcium alginate (different proportions) are possible. This alginate matrix imparts a cohesive structure to the dressing and has mechanical properties suitable for protecting a wound while remaining flexible. The amount of alginate incorporated in the preparation varies from 1% wt to 4% wt according to the type used.

Processes for making alginates salts, sodium or calcium, are well known in the art. For example, such processes are described in GB-A-0415042 and GB-A-0568177. Two main factors are considered in the preparation of the alginate matrix: firstly, the capacity of alginate to react with calcium or sodium species and secondly, the viscosity of the resulting mixture. The viscosity of the resulting mixture (sodium or calcium alginate or a combination thereof) is directly dependent upon the extent of this reaction. The greater the reactivity (salt formation) between alginate and sodium or calcium species, the less alginate is required in the production of the dressing.

The other components of the dressing of the present invention may be advantageously loaded in the hydrogel by absorption of solutions or slurries containing these ingredients or by direct deposition on the external surface of the hydrogel.

One component is a hydrocolloid component which retains moisture in the hydrogel and gives the hydrogel tissue adherence qualities. This is advantageous because moisture in the hydrogel retains the mechanical properties, such as flexibility, of the hydrogel. Tissue adherence is also beneficial since it allows the hydrogel of the present invention to be used directly on wounds without adhesive tape or superimposed bandages. Examples of suitable hydrocolloids are carboxymethylcellulose, pectine and gums. The hydrogel of the present invention will preferably contain about up to 4 to 5% wt of a hydrocolloid other than carboxymethylcellulose, but it is most preferred to keep the hydrocolloid concentration at values less than 1% in order to avoid diminishing the cohesiveness of the hydrogel.

The salt component absorbed in the hydrogel can be selected from sodium, magnesium, silver or other therapeutically acceptable salts or combinations thereof. These salts have advantageous disinfectant properties and various wound healing properties. Preferably, a 4t% wt sodium chloride solution consisting of sterilized sea salt is loaded in the hydrogel. It is however possible to increase the sea salt concentration to levels up to 8 to 10% wt or to keep it as low as 0.9% wt (physiological solution). The latter concentration has diminished anti-bacterial properties when compared to higher concentrations whereas a strongly concentrated solution can cause a burning sensation.

The vulnerary polysaccharide component absorbed in the hydrogel is preferably chitin, chitosane or a chitosane derivative. Chitin and chitosanes incorporate various sought after properties essential in the healing process of wounds. They have absorbent properties for wicking exudates from the wound site, maintain desired humidity levels at the wound site, and have disinfectant as well as anti-neoplastic properties, that is, they favor the organized formation of new cells which in turn leads to the formation of more esthetically pleasing scars. Chitosane derivatives such as carboxymethylchitosane can also be used, however the concentrations and application conditions will be different in accordance with their efficiency and their characteristics. Preferably, the vulnerary polysaccharide component is chitosane and is absorbed in the hydrogel as a 0.5 to about 1% wt solution in a 1 N lactic acid solution. The required concentration can be superior or inferior depending on the resulting viscosity of the chitosane-lactic acid solution and the anti-bacterial efficiency of the chitosane component. A viscosity that is too high renders the absorption of the chitosane component in the hydrogel difficult. One way to overcome this problem is to dip the hydrogel in the chitosane component solution and to have it evaporate on the surface of the hydrogel.

The further disinfectant component can be chosen from a variety of suitable disinfectants, which will not cause wound irritation or systemic toxicity. Preferred disinfectants are organic acids such as citric acid, dilute acetic acid, benzoic acid, proprionic acid and alcohols such as isopropanol or ethanol. Other examples of possible disinfectants are chlorinated phenolics such as "TCP" (2,4,6-trichlorophenol); pine disinfectants such as terpineol; biguanides such as chlorhexidine (when mixed with cetrimide), chlorhexidine gluconate or chlorhexidine acetate; surfactants, preferably amphotheric surfactants; aldehydes such as formaldehyde or gluteraldehyde; halogens such as iodine; iodophores (iodine-containing compounds that slowly liberate inorganic iodine) or organic iodine such as polyvidone-iodine; peroxides and other oxygenators; aluminum zinc agents such as aluminum acetate or zinc sulfate; furan derivatives and, finally, quinoline derivatives such as clioquinol. The disinfectant is either loaded by absorption in the hydrogel or by evaporation thereon. The proportion of disinfectant(s) used will of course depend on the chosen disinfectant(s), their strength, activity and toxicity.

Other optional ingredients having wound healing or anesthetic properties can also be added to the formulation. For example, various vitamins and amino-acids could be incorporated in the hydrogel to diminish scarring. Common anesthetics such as novocaine, lidocaine and derivatives thereof could also be incorporated in the hydrogel. The proportion of these optional ingredients will vary according to the advantages and characteristics sought after in the wound dressing.

EXAMPLE 1

A hydrogel dressing in accordance with the present invention was prepared as follows:

A paste is prepared according to the following formulation and procedure:

| | |
|---|---|
| sodium/calcium alginate (average viscosity): | 4% |
| carboxymethyl cellulose: | 1.5% |
| water: | 93% |
| sea salt: | 1.5% |

Sea salt is entirely dissolved in water. Alginate and carboxymethyl cellulose are mixed together. The mixture is then gradually sprinkled into the sea salt containing water solution while stirring vigorously (mechanical blender), until the mixture is dissolved and homogeneously distributed. The resulting paste is either used immediately or later, depending on the delay required for the paste to reach its desired viscosity, which can vary according to the type of alginate used.

An aqueous 2% calcium chloride solution is poured into a mould and vaporized to form a thin film covering the mould's entire surface. The paste is uniformly poured into the mould in accordance with the desired thickness (for example 2 mm). A 2% calcium chloride solution is then vaporized on the surface to cover the entire paste (until surface run-off). The resulting gel is removed from the mould and is soaked in a reservoir containing an aqueous calcium chloride solution (2%). The soaking time used in this trial was 3 minutes but can be of longer or shorter duration, in accordance with the desired cohesion and resistance.

The dressing is then transferred to a dryer at 50° C. in order to reduce the water content to about 50% or another concentration, according to desired product characteristics, which mainly include flexibility and malleability.

The dressing is sprayed with a 0.5% chitosane solution, in lactic acid (0.1N) or another organic acid. The dressing is then dried until the shiny appearance at the surface of the product has disappeared.

The dressing is transferred to its packaging and sterilized by irradiation at 27 to 36 kGy for 5.5 hours. The final composition of the dried product is:

| | |
|---|---|
| sodium/calcium alginate (average viscosity): | 28.6% |
| carboxymethyl cellulose: | 10.7% |
| water: | 50% |
| sea salt: | 10.7% |

EXAMPLE 2

Same as Example 1, with sprayed on disinfectant; ethanol.

Although the invention has been described above with respect to one specific form, it will be evident to a person skilled in the art that it may be modified and refined in various ways. It is therefore wished to have it understood that the present invention should not be limited in scope, except by the terms of the following claims. It is also the intention that all possible variants, whether presently known or unknown, that do not have a direct and material effect on the way the invention works, are to be covered by the following claims.

What is claimed is:

1. A disinfectant wound dressing for treating tissue wounds, said dressing consisting essentially of a hydrogel matrix including an absorbent fibrous material comprising alginate salt, said hydrogel matrix being loaded with material comprising:
    a hydrocolloid moisture retaining component selected from the materials consisting of carboxymethyl cellulose, gelatin, and mixtures thereof said materials being present in a proportion of between more than 0 wt % to about 1 wt % calculated on a dry basis;
    a hypertonic salt component selected from the group consisting of sea salt, sodium salts, magnesium salts, silver salts and combinations thereof, said salt component being present in a proportion of more than 4.5 wt % and up to 50 wt % calculated on a dry basis, said salt component being compatible with the tissue being treated and acting as a disinfectant; and
    a vulnerary polysacharide component being therapeutically acceptable with regard to wound tissue irritation level and systemic toxicity level.

2. A wound dressing as defined in claim 1, wherein said alginate salt is selected from the group consisting of sodium alginate, calcium alginate and mixtures thereof.

3. A wound dressing as defined in claim 1 wherein said vulnerary polysaccharide component is selected from the group consisting of chitin, chitosane and derivatives thereof.

4. A disinfectant wound dressing for treating tissue wounds, said dressing consisting essentially of an anesthetic compound and a hydrogel matrix including an absorbent fibrous material comprising alginate salt, said hydrogel matrix being loaded with material comprising:
    a hydrocolloid moisture retaining compound selected from the materials consisting of carboxymethyl cellulose, gelatin, and mixtures thereof said materials being present in a proportion of between more than 0 wt% and about 1 wt % calculated on a dry basis'
    a hypertonic salt component selected from the group consisting of sea salt, sodium salts, magnesium salts, silver salts, and combinations thereof, said salt component being present in a proportion of more than 4.5 wt % and up to 50 wt % calculated on a dry basis, said salt component being compatible with the tissue being treated and acting as a disinfectant; and
    a vulnerary polysaccharide component being therapeutically acceptable with regard to wound tissue irritation level and systemic toxicity level.

5. A disinfectant wound dressing for treating tissue wounds, said dressing consisting essentially of a hydrogel matrix including an absorbent fibrous material comprising alginate salt, said hydrogel matrix being loaded with material comprising:
    a hydrocolloid moisture retaining compound selected from the materials consisting of carboxymethyl cellulose, gelatin, and mixtures thereof said materials being present in a proportion of between more than 0 wt % and about 1 wt % calculated on a dry basis'
    a hypertonic salt component selected from the group consisting of sea salt, sodium salts, magnesium salts, silver salts, and combinations thereof, said salt component being present in a proportion of more than 4.5 wt % and up to 50 wt % calculated on a dry basis, said salt component being compatible with the tissue being treated and acting as a disinfectant;
    a second disinfectant component selected from the materials consisting of organic acids, chlorinated phenolics, terpineols, biguanides, quaternary ammonium compounds, surfactants, aldehydes, halogens, peroxides and other oxygenators, aluminum zinc compounds, furan derivatives and quinoline derivatives, and mixtures thereof; and
    a vulnerary polysaccharide component being therapeutically acceptable with regard to wound tissue irritation level and systemic toxicity level.

* * * * *